(12) United States Patent
Fuchs (10) Patent No.: US 7,950,391 B2
(45) Date of Patent: May 31, 2011

(54) DISPENSER AND DOSING SUBASSEMBLY FOR DOSING OF A MEDIUM

(75) Inventor: Karl-Heinz Fuchs, Radolfzell (DE)

(73) Assignee: Ing. Erich Pfeiffer GmbH, Radolfzell (DE)

(*) Notice: Subject to any disclaimer, the term of this patent is extended or adjusted under 35 U.S.C. 154(b) by 1206 days.

(21) Appl. No.: 11/601,594

(22) Filed: Nov. 17, 2006

(65) Prior Publication Data

US 2007/0113841 A1    May 24, 2007

(30) Foreign Application Priority Data

Nov. 21, 2005 (DE) .................. 10 2005 056 488

(51) Int. Cl.
*A61M 16/00* (2006.01)
*A62B 9/02* (2006.01)

(52) U.S. Cl. .................. 128/205.13; 128/205.24

(58) Field of Classification Search ............. 128/205.13, 128/200.11, 200.14, 200.21, 200.22, 200.24, 128/203.12, 203.15, 203.16; 604/295
See application file for complete search history.

(56) References Cited

U.S. PATENT DOCUMENTS

| | | | | |
|---|---|---|---|---|
| 3,335,913 | A | * | 8/1967 | Bouet .......................... 222/95 |
| 4,147,282 | A | | 4/1979 | Levy |
| 5,069,204 | A | | 12/1991 | Smith et al. |
| 5,265,770 | A | | 11/1993 | Matkovich et al. |
| 5,664,704 | A | | 9/1997 | Meadows et al. |
| RE37,675 | E | * | 4/2002 | Gueret ...................... 222/153.06 |
| 2006/0079851 | A1 | * | 4/2006 | Guerrieri ...................... 604/295 |

FOREIGN PATENT DOCUMENTS

| | | |
|---|---|---|
| DE | 1 482 675 | 7/1969 |
| DE | 28 22 115 | 12/1978 |
| DE | 3217913 A1 | 12/1983 |
| DE | 91 01 305.4 | 6/1991 |
| DE | 40 35 290 A1 | 5/1992 |
| DE | 43 32 869 A1 | 4/1995 |
| EP | 0 079 326 | 5/1983 |
| EP | 0 388 741 A1 | 9/1990 |
| EP | 1 136 387 A1 | 9/2001 |
| EP | 1 213 003 A1 | 6/2002 |
| FR | 2 206 741 | 6/1974 |
| FR | 2 709 734 | 3/1995 |
| GB | 726756 | 3/1955 |
| GB | 1 449 504 | 9/1976 |

OTHER PUBLICATIONS

German Patent Office Search Report dated Feb. 17, 2006 (4 pages).

* cited by examiner

*Primary Examiner* — Patricia M Bianco
*Assistant Examiner* — Ophelia Hawthorne
(74) *Attorney, Agent, or Firm* — Flynn, Thiel, Boutell & Tanis, P.C.

(57) ABSTRACT

A dispenser for a liquid or pulverulent, in particular a pharmaceutical medium with a medium reservoir, is provided for single-handed operation. The dispenser includes a dosing opening and is bounded in some sections by wall sections of flexible design, and by a dimensionally stable holding plate, which is provided as a handle for the application of actuating forces to the medium reservoir.

14 Claims, 4 Drawing Sheets

DISPENSER AND DOSING SUBASSEMBLY FOR DOSING OF A MEDIUM

FIELD OF THE INVENTION

The invention relates to a dispenser for dosing of at least one liquid or pulverulent medium and a dosing subassembly for a dispenser of this type.

BACKGROUND OF THE INVENTION

Dispensers which are provided for dosing of liquid or pulverulent media, in particular of pharmaceutically active substances and which permit manual dosing of the medium accommodated in a medium reservoir are known from the prior art. Dispensers of this type permit dosing of a medium in the form of drops, droplet mist or powder mist, and are used in particular in order to insert media into natural body orifices, such as eyes, ears or nose. It is known in particular from the prior art to design a dispenser of this type as a pipette for nose drops, as a squeezable bottle for eye or ear drops or as a compressible plastic ampul for single dosing of media. The dispensers known from the prior art are unfavorable to handle especially for the administration of eye drops, since they require considerable operating forces and, in view of a generally slim, substantially cylindrical geometry, are only inadequately suitable for precisely targeted dosing and application of the medium.

The object of the invention is to provide a dispenser and dosing subassembly which permit more precise dosing and simple handling, in particular for administering eye drops.

This object is achieved, according to a first aspect of the invention, by a dispenser of the type mentioned at the beginning which has a medium reservoir provided for single-handed operation, the medium reservoir having at least one dosing opening and being bounded at least in some sections by wall sections of flexible design and by at least one dimensionally stable holding plate which is provided as a handle for the application of actuating forces to the medium reservoir. Single-handed operability of a dispenser means that the dispenser is typically held between thumb and index finger and is compressed by exertion of an actuating force. The medium accommodated and stored in the medium reservoir is therefore pressurized and can be discharged through a dosing opening assigned to the medium reservoir, i.e. the medium can be dispensed into the surroundings of the dispenser. The dosing opening has a narrow cross section, in particular a nozzle cross section matched to the viscosity of the medium accommodated in the medium reservoir. In a preferred embodiment, which is provided for dosing of an aqueous medium, the dosing opening has a conical cross section with an average diameter of approx. 1.1 mm, a length of approx. 1.4 mm and a cone angle of 30 degrees. In a particularly preferred embodiment of the invention, an average diameter of 0.8 mm, a length of 1.4 mm and a cone angle of 30 degrees are provided for the dosing opening.

The medium reservoir is configured for operation with low operating forces, for which reason medium reservoir wall sections of flexible design are provided which can easily be deformed, even when subjected to small actuating forces, in order to permit the desired build up of pressure in the medium reservoir. In order to ensure simple actuation of the dispenser, at least one dimensionally stable holding plate is provided, which serves as an abutment for the actuating forces to be applied. The holding plate also permits secure gripping of the dispenser, thus ensuring targeted dosing of the medium to be discharged, in particular into a dispenser user's eye.

In a refinement of the invention, it is provided that the dosing opening is formed on a dosing nozzle, the center longitudinal axis of which is arranged at an angle of 15 degrees to 55 degrees to an outer surface of the holding plate, in order to ensure ergonomic handling of the dispenser. The dispensing nozzle is an extension which, in particular, is of elongate design and is formed on the holding plate in a raised manner. The dosing nozzle has a center longitudinal axis which, for example in the case of a cylindrical design of the dosing nozzle, corresponds to the cylinder axis. The center longitudinal axis takes up an angle of 15 degrees to 55 degrees with an outer surface of the holding plate, which can be approximately described by a plane approximate to the holding plate. This orientation of the dosing nozzle makes it possible for a user to orient the holding plate parallel to the area of the face adjacent to the eye, in order to achieve favorable dosing of the medium into the eye. Since, during the dosing operation, the user can rest his hand on the area of the face, the dosing opening, which is formed in particular on the end side of the dosing nozzle, can be brought closer to the eye in a readily controllable manner. The dosing nozzle is in this case preferably of taper design in an end region in which the dosing opening is provided, so that it only partially covers a field of view of the eye to be acted upon by the medium. Adequate control of the dosing operation is therefore possible, for example with a mirror. In the case, in particular, of a cylindrical design, the dosing nozzle preferably has a diameter of less than 20 mm, particularly preferably less than 15 mm. In a preferred embodiment of the invention, the center longitudinal axis of the dosing nozzle and the outer surface of the holding plate enclose an angle of 25 degrees to 45 degrees. In a particularly preferred embodiment of the invention, an angle of 35 degrees is provided between the center longitudinal axis and outer surface. The dosing opening is advantageously arranged on the end side of the center longitudinal axis of the dosing nozzle. However, the dosing opening, instead of being arranged on the center longitudinal axis, may also be arranged on the typically spherically or conically tapered end region of the dosing nozzle.

In a further refinement of the invention, it is provided that the flexible medium reservoir is bounded by two dimensionally stable holding plates arranged opposite each other, with the dosing nozzle being assigned to one of the holding plates. By means of the two dimensionally stable holding plates which lie opposite each other and in particular are oriented substantially parallel to each other, particularly readily controllable application of actuating forces to the dispenser is possible. Both holding plates can easily be gripped, thus ensuring a defined transmission of force to the flexible medium reservoir arranged in between. The two dimensionally stable holding plates can be connected to each other exclusively by the wall sections, which are of flexible design, of the medium reservoir. However, an additional connection between the holding plates via hinge devices, in particular fixed body hinges, is also conceivable, in order to ensure additional stabilization of the flexible medium reservoir and facilitation of the operation to actuate the dispenser. The dosing nozzle is assigned to one of the holding plates and therefore, when the dispenser is actuated, is not displaced or pivoted in its orientation with respect to the target to be acted upon with the medium, in particular an eye, by deformation effects of the wall sections, which are of flexible design, of the medium reservoir.

In a further refinement of the invention, it is provided that the dosing opening is provided in a separate dosing subassembly, which can be fitted on the dosing nozzle, which is assigned to the holding plate and is designed as a receiving shaft. The design of a separate dosing subassembly comprising the dosing opening firstly permits favorable production of the medium reservoir provided with the holding plates, which can be produced in particular in a plastics injection molding technique or plastics blow molding technique. Secondly, the separate dosing subassembly makes it possible for the dispenser to be able to be adapted in a simple manner to different liquid media, in particular of high or low viscosity, or to pulverulent media. A modular manner of constructing the dispenser with the medium reservoir and the holding plates, on the one hand, and the dosing subassembly, on the other hand, ensures that it can be adapted to properties of the medium to be discharged, in particular to the viscosity of the medium to be discharged. To fit the dosing subassembly on the medium reservoir, the dosing nozzle is designed as a receiving shaft, so that the dosing subassembly can be fitted on the dosing nozzle by an installation operation with a form fit, frictional fit or cohesive material joint or by a combination thereof. The dosing nozzle may in particular have a sleeve-shaped geometry into which the dosing subassembly can be pushed and locked. The dosing subassembly completely closes the dosing nozzle apart from the dosing opening and medium can only emerge through the dosing opening.

In a further refinement of the invention, it is provided that at least one latching device for locking the dosing subassembly with a form fit is provided in the dosing nozzle designed as a receiving shaft. The latching device makes it possible for the dosing subassembly to be locked in the dosing nozzle with a form fit. For this purpose, correspondingly designed latching geometries, such as latching lugs and undercuts, are to be provided on the dosing nozzle and the dosing subassembly and, when the dosing subassembly is installed in the dosing nozzle, can enter into operative connection with each other with a form fit. Installation of the dosing subassembly in the dosing nozzle in a simple manner which is uncritical with regard to manufacturing tolerances of the dosing nozzle and the dosing subassembly can therefore be ensured. In a preferred embodiment of the invention, at least one centrally arranged latching device for locking the dosing subassembly with a form fit is provided. The centrally arranged latching device lies on the center longitudinal axis or at least adjacent to the center longitudinal axis of the dosing nozzle and permits an advantageous transmission of holding forces between the dosing nozzle and the dosing subassembly.

In a further refinement of the invention, it is provided that the latching device has at least one latching geometry on an inner surface and/or an outer surface of the dosing nozzle and a latching pin arranged coaxially with respect to the center longitudinal axis of the dosing nozzle, the latching geometry and latching pin being provided for centering and fixing the dosing subassembly. Reliable locking of the dosing subassembly on the dosing nozzle can therefore be ensured. The latching geometry on the inner surface and/or the outer surface of the dosing nozzle permits a medium-tight fitting of the dosing subassembly into the dosing nozzle and, in addition to the latching geometries designed as latching lugs and of undercut design, can also have a sealing device, in particular of encircling design, thus preventing medium from being able to emerge between dosing subassembly and dosing nozzle. Additional locking of the dosing subassembly is made possible by the latching pin, which is arranged coaxially with respect to the center longitudinal axis of the dosing nozzle, the latching pin and a latching geometry, which is provided in a corresponding manner on the dosing subassembly and is designed in particular in the form of an arrangement of latching lugs, permitting a particularly advantageous, centered transmission of force between dosing nozzle and dosing subassembly.

In a further refinement of the invention, it is provided that the dosing subassembly has a spring-loaded outlet valve, which is provided for temporarily closing the dosing opening. By means of a spring-loaded outlet valve, which, in particular, has a valve pin provided for closing the dosing opening, and at least one valve spring assigned to the valve pin, medium can be prevented from emerging from the medium reservoir in a rest state of the dispenser. Likewise, penetration of contamination from the surroundings of the medium reservoir through the dosing opening into the medium can be avoided. In one embodiment of the invention, it is provided that, in order to remove the temporary closure of the dosing opening, the spring-loaded outlet valve is coupled to a forced guidance device which is activated upon a relative movement of the two holding plates of the medium reservoir and applies an opening force for the outlet valve counter to the static prestressing of the valve spring. In a preferred embodiment of the invention, it is provided that the valve pin is assigned a plunger sleeve which, in a sealing manner, closes a dosing chamber bounded by the dosing nozzle and the dosing subassembly and which, as the pressure of the medium rises in the dosing chamber, permits the valve pin to be driven out counter to the prestressing of the valve spring. In a particularly preferred embodiment of the invention, an average diameter of 0.8 mm, a length of 1.4 mm and a cone angle of 30 degrees is provided for the dosing opening, and a cone angle of 20 degrees is provided for the valve pin. This results in a sealing length of approx. 0.2 mm between dosing opening and valve pin ensuring, in consideration of the valve spring forces acting on the valve pin, a microbiologically tight sealing of the medium reservoir with respect to the surroundings. The surface pressure, i.e. the force acting on a surface unit, between the dosing opening and valve pin subassemblies is at least 3 N/mm$^2$, preferably at least 5 N/mm$^2$ particularly preferably at least 6 N/mm$^2$. The effect which can therefore be achieved is that the materials of the dosing opening and/or of the valve pin are compressed close to their yield point in the region in which they are in contact with the respectively opposite subassembly, and therefore surface roughnesses are also deformed in such a manner that microbiological tightness can be ensured.

In a further refinement of the invention, it is provided that a dimensionally stable collar for coupling of the holding plate is provided on a peripheral edge region of a wall section, which is of flexible design, of the medium reservoir, which edge region faces the dimensionally stable holding plate. The dimensionally stable collar is molded integrally onto the wall section of flexible design and permits installation of the flexible wall section on the holding plate. In a preferred embodiment of the invention, the wall section of flexible design is essentially designed in the form of a sleeve or in the manner of a bellows and has a circularly encircling, dimensionally stable collar which can be fitted on a correspondingly shaped receiving geometry of the holding plate.

In a further refinement of the invention, it is provided that a peripheral holding ring is provided for coupling of the holding plate to the dimensionally stable collar with a form fit, the holding ring engaging around the holding plate and the collar in each case in an end region and coupling them to each other in a sealing manner. The holding ring therefore permits coupling, with a form fit, between the holding plate and the dimensionally stable collar of the wall section, which is of flexible design, of the medium reservoir, thus making it possible to provide a medium-tight connection. The holding ring, which can be adapted to the contours of the holding plate and the encircling collar and can be of annular design, in particular circular-ring-shaped design, in a connecting plane between holding plate and encircling collar, has a substantially U-shaped cross section in a cross-sectional plane oriented orthogonally with respect to the connecting plane, with the end regions of the holding plate and of the encircling collar being able to be received and clamped between limbs of the U-shaped cross section in order to ensure the desired sealing connection. The holding ring may be snapped as a separate component onto the collar and the holding plate pressed onto it. In a preferred embodiment of the invention, the collar and the holding plate are encapsulated in the plastics injection molding process by the holding ring.

In a further refinement of the invention, it is provided that the holding plate and the dimensionally stable collar are provided with a reduced wall thickness in the end region in order, when molding on the holding ring in the plastics injection molding process, to bring about an intimate connection, in particular connection with a cohesive material joint, between the holding ring and the end regions. The reduced wall thickness of the dimensionally stable collar and of the holding plate in the end region can be configured in such a manner that, when the holding ring is molded onto the encircling collar and the end region of the holding plate, which can be accommodated together in a plastics injection mold, local melting of the end regions of the holding plate and the encircling collar occurs when the heated plastics material for the holding ring is introduced. A cohesive material joint between the holding ring, the encircling collar and the holding plate can therefore be achieved. Thermal welding of the encircling collar to the holding plate would also be conceivable, but, for this purpose, unlike the encapsulation by a holding ring by injection molding, complicated measures have to be taken in order to ensure a visually attractive surface after the thermal welding has been carried out. Ultrasonic welding between the encircling collar and the holding plate is likewise a possibility, but is less suitable in particular for use of the dispenser for eye drops, since, during the ultrasonic welding operation, extremely small particles are produced which are subsequently carried by the medium into the eye at the application point.

In a further refinement of the invention, it is provided that wall sections, which are of flexible design, of the medium reservoir are produced at least in some sections as a bellows with a wall thickness of 0.1 mm to 0.6 mm from a plastics material. By means of a design as a bellows, i.e. by means of a sequence of rings which are arranged in an alternating manner and are in the shape of conical sections, particularly advantageous flexibility of the wall sections, which are of flexible design, of the medium reservoir can be achieved. The design as a bellows ensures a structurally readily predeterminable direction of deformation of the medium reservoir when actuating forces are applied to the holding plates, so that a uniform dosing operation can be ensured. In a preferred embodiment of the invention, the wall thickness of the wall sections, which are of flexible design, of the medium reservoir is 0.25 mm to 0.5 mm, and, in particular, polyethylene is provided as the plastics material for the bellows. Hinge zones which are designed in particular with a wall thickness of 30% to 70%, preferably 40% to 60%, particularly preferably 50%, of the wall thickness of the wall sections, which are of flexible design, of the medium reservoir can be provided in the connecting regions between the rings in the form of conical sections.

In a further refinement of the invention, it is provided that the flexible medium reservoir is provided at least in some sections with a water vapor barrier layer on an inner and/or outer surface. This ensures that the concentration of the medium which is accommodated in the medium reservoir and typically has a considerable proportion of water is not changed by water escaping in the form of water vapor, even if the dispenser is stored for relatively long periods. By contrast, for pulverulent media, which typically have a small proportion of water, the water vapor barrier layer is provided to secure the small content of water in order to prevent the pulverulent medium from swelling or forming lumps. The water vapor barrier layer can be provided in particular in the region of the bellows, i.e. at a point where the medium reservoir only has a small wall thickness and there could be a high penetration rate for water vapor, in order to ensure a low water vapor diffusion rate in these regions. The water vapor barrier layer, which can be designed in particular as a silicon oxide coating or as a poly-para-xylylene coating, is in particular applied to the medium reservoir from the outside and/or from the inside. For example, a plasma coating process can be used to coat the medium reservoir with the water vapor barrier layer.

In a further refinement of the invention, it is provided that a drip edge for conducting away drops of medium without any residue is provided on the dosing nozzle or the dosing subassembly in the region of the dosing opening. The drip edge promotes the formation of a drop of medium during the dosing operation and, as the drop of medium is dispensed, prevents relatively large quantities of medium from remaining behind. As a result, contamination in the region of the dosing opening of the dispenser by medium which has remained can be avoided. The drip edge can be arranged in particular annularly around the dosing opening and can be provided with a tapering cross section in order to ensure that the discharged medium flows away at least substantially without any residue.

In a development of the dispenser, pressure equalizing means which permit ambient air to flow into the media reservoir are provided, the pressure equalizing means preferably being arranged in a wall region of the media reservoir in such a manner that they are surrounded on the media reservoir side by medium when the dispenser is actuated.

The pressure equalizing means makes it possible that, after an actuation, the volume of the discharged medium can be equalized with air, thus avoiding a permanent negative pressure in the media reservoir. The pressure equalizing means are to be designed in such a manner that, when the dispenser is actuated, the pressure equalizing means do not lose pressure or only lose it to a small extent. When a pressure equalizing means is used with a filtering membrane, this can be ensured by the membrane only permitting a small throughflow quantity per unit of time, so that, although air can flow in in an uncritical manner in terms of time after the actuation, a dissipation of the pressure built up by the actuation does not take place to a relevant extent. In this case, the configuration of the membrane as a hydrophobic membrane is particularly advantageous. In an appropriate arrangement, in which the membrane is surrounded on the medium reservoir side by medium when there is an actuation, this prevents medium from emerging through the membrane. The pressure equalizing means can be provided both in the wall of the media reservoir itself, for example in one of the holding plates, and in a wall section of the dosing subassembly that bounds the media reservoir with respect to the dosing subassembly.

In a development of the dispenser, the pressure equalizing means have a filtering membrane preferably filtering microbiological impurities.

The object on which the invention is based is achieved, according to a second aspect, by a dosing subassembly with a valve housing which is penetrated in a wall region by a dosing opening, which can be closed by a valve pin accommodated in the valve housing, the valve pin being assigned a plunger sleeve and a spring device, with an active surface of the plunger sleeve being at least 50 times larger than a cross-sectional area of the dosing opening. The valve housing can be designed in particular in the form of a sleeve and, on an end region of the sleeve, can be provided with a wall section which is shaped spherically or conically in some sections and is penetrated by the dosing opening. A dosing chamber is closed off by the wall regions of the valve housing and by the plunger sleeve and receives the medium to be discharged directly before the medium is discharged. The dosing opening therefore produces a communicating connection between the dosing chamber and the surroundings. The plunger sleeve has a hydraulically effective active surface on which an opening force acts when the medium accommodated in the dosing chamber is pressurized. The opening force is at least substantially opposed by the valve closing force applied by the spring device. By means of the extreme ratio of the active surface of the plunger sleeve, on the one hand, and of the cross-sectional area of the dosing opening, on the one hand, reliable opening up of the dosing opening can be achieved by the valve pin even at a low pressure of the medium and high closing force of the spring device. The spring device is designed to apply a high valve closing force in order to ensure that the valve pin can reliably, in particular microbiologically tightly, close the dosing opening between two dosing operations and can virtually eliminate any penetration of contaminations from the surroundings of the dispenser into the medium reservoir. In this case, it is provided that a surface pressure of at least 3 $N/mm^2$, preferably at least 5 $N/mm^2$, particularly preferably at least 6 $N/mm^2$, is achieved between the valve pin and the dosing opening. An opening of the valve device is provided at a pressure of 0.5 bar which is applied by an actuating force being exerted on the holding plate by a user.

In a preferred embodiment of the invention, the active surface of the plunger sleeve is at least 100 times larger than the cross-sectional area of the dosing opening. In a particularly preferred embodiment of the invention, the active surface of the plunger sleeve is at least 200 times larger than the cross-sectional area of the dosing opening. Here, the spring device can be designed in particular as a spiral spring or coiled spring and can be produced from a plastic or a metallic material.

In a further refinement of the invention, it is provided that the valve pin is designed in such a manner that it at least virtually completely fills the dosing opening in the closed state. This makes it possible to minimize or entirely avoid a volume of medium remaining on the outside of the dosing opening after the dosing operation has been carried out. Contaminations, such as they may occur in particular due to residues of liquid in the region of the dosing opening, can thereby be effectively reduced or prevented. The risk of contaminations penetrating into the medium reservoir can therefore also be reduced as a result. Although contaminations of this type can be prevented in the rest state of the dispenser because of the microbiologically tight dosing valve, a contamination of the medium reservoir is conceivable because of backflow effects, such as may occur in the region of the dosing opening during the dosing operation. In a preferred embodiment of the invention, the dosing opening is designed as a conical bore, and the dosing pin has a conical extension which is provided on the end side and completely fills the dosing opening in the closed state. Advantageous sealing action can be obtained with the conical design of the dosing opening and of the dosing pin. In addition, a favorable opening characteristic of the dosing valve can also be achieved as a result, since, during opening of the valve gap between dosing opening and valve pin, a force opposing the closing force because of the pressurized medium acts on the conical extension of the valve pin, which assists further opening of the valve gap. In a preferred embodiment of the invention, the valve pin closes the dosing opening at least virtually flush with an outer surface of the valve housing, so that, when the valve is closed, excess medium is injected onto the outer surface of the valve housing where it can either be evaporated or wiped away, so that only a small quantity of medium, if any at all, which would lead to the valve housing being contaminated in the region of the dosing opening, remains. In a particularly preferred embodiment of the invention, different cone angles are provided for the dosing opening and the valve pin, with the cone angle of the valve pin being selected to be smaller than the cone angle of the dosing opening. As a result, a virtually complete filling of the dosing opening by the valve pin with a small sealing length can be achieved. The sealing length results from the touching contact between valve pin and dosing opening, with there being, in particular, an annular line-shaped contact. In view of the spring force of the valve spring, a short sealing length means a high surface pressure and therefore ensures good microbiological sealing of the dosing opening.

In a development of the dosing subassembly, a throttle which reduces a volumetric flow from a media reservoir to the dosing opening is mounted upstream of the dosing opening.

A throttle of this type prevents medium from flowing too rapidly from the medium reservoir into the dosing subassembly and from there through the dosing opening after the dosing opening is opened. This prevents a discharge of too much medium by too high a force upon actuation. One possibility for realizing this throttle is a simple aperture between the dosing subassembly and the media reservoir, the diameter of which is selected to be sufficiently small. The diameter is to be defined as a function of the viscosity of the medium and the intended application. For most applications and for viscosities customary for eye drops, diameters of between 0.1 mm and 0.5 mm are particularly expedient.

In a development of the dosing subassembly, the throttle is designed as a capillary tube.

In such a configuration, the throttle is formed by an additional component in the form of a capillary tube. During the installation, this is inserted into a receptacle, provided for it, of the dosing subassembly. This is advantageous, since, as a result, the manufacturing of the dosing subassembly is simpler and, in addition, a particularly simple adaptation of the throttling action can be achieved by selecting a suitable capillary tube. Capillary tubes with capillary openings with diameters of between 0.1 mm and 0.5 mm and a length of between 2 mm and 4 mm constitute a preferred embodiment.

BRIEF DESCRIPTION OF THE DRAWINGS

Further advantages and features of the invention emerge from the claims and from the description below of a preferred exemplary embodiment of the invention, which is illustrated with reference to drawings, in which:

DETAILED DESCRIPTION

Figure 1:
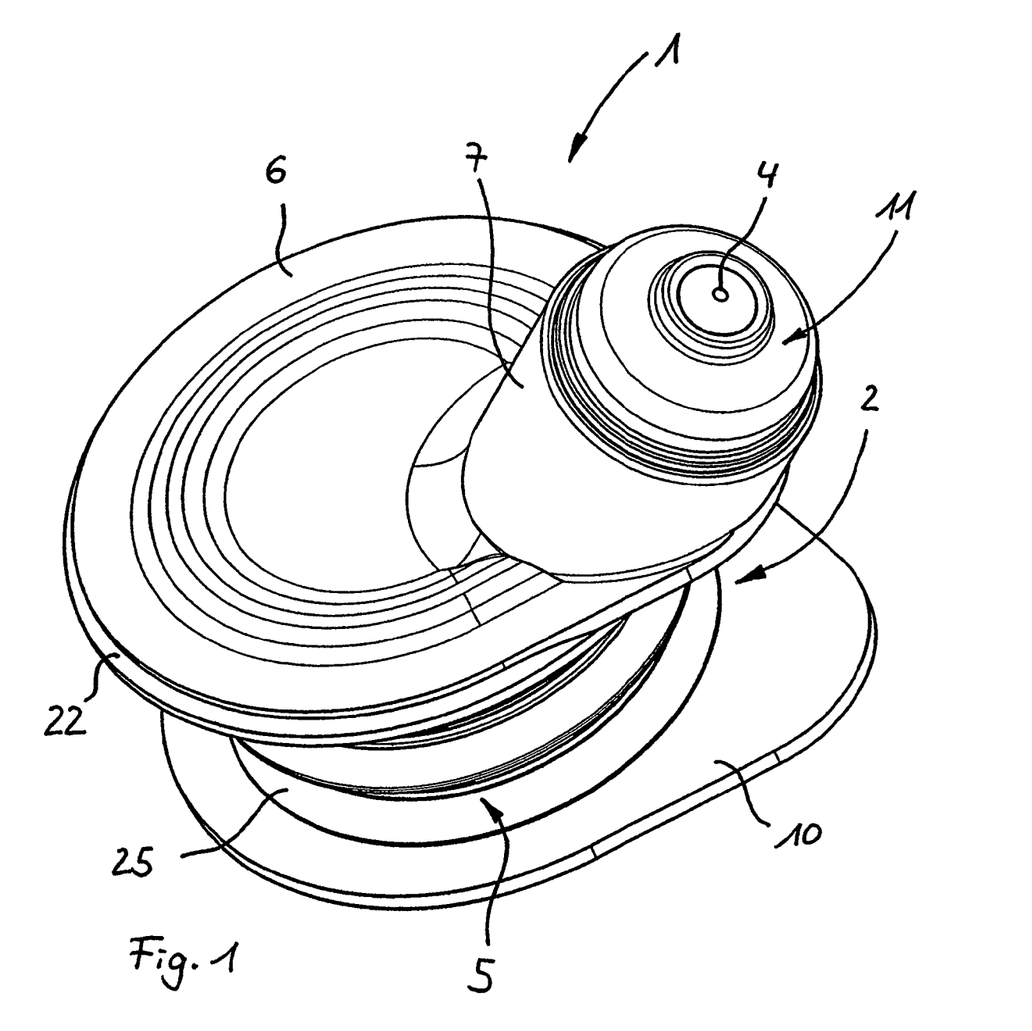
FIG. 1 shows a perspective illustration of a first embodiment of a dispenser according to the invention with a flexible medium reservoir accommodated between two dimensionally stable holding plates, and with a dosing nozzle, which is provided on the one holding plate, with a dosing subassembly.
Figure 2:
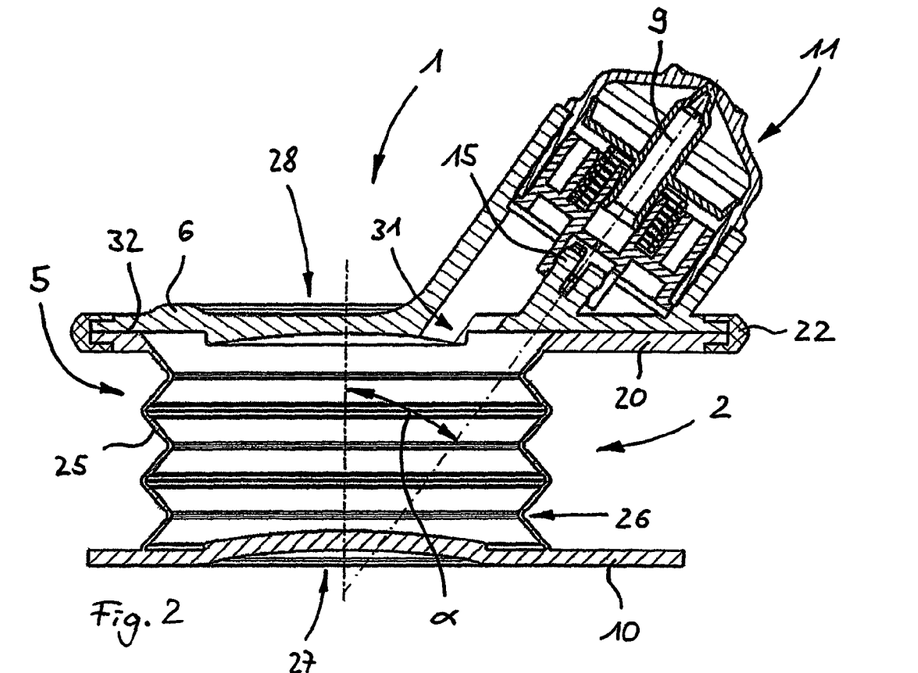
FIG. 2 shows, in a sectional illustration, the dispenser according to FIG. 1.
Figure 3:
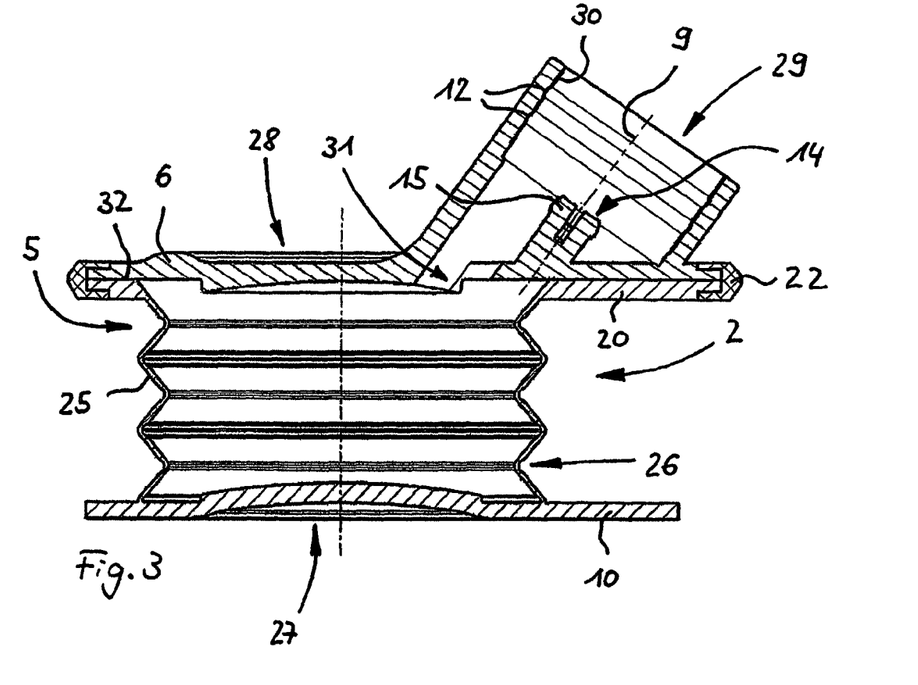
FIG. 3 shows, in a sectional illustration, the medium reservoir with the holding plates according to FIG. 2.
Figures 4, 5:
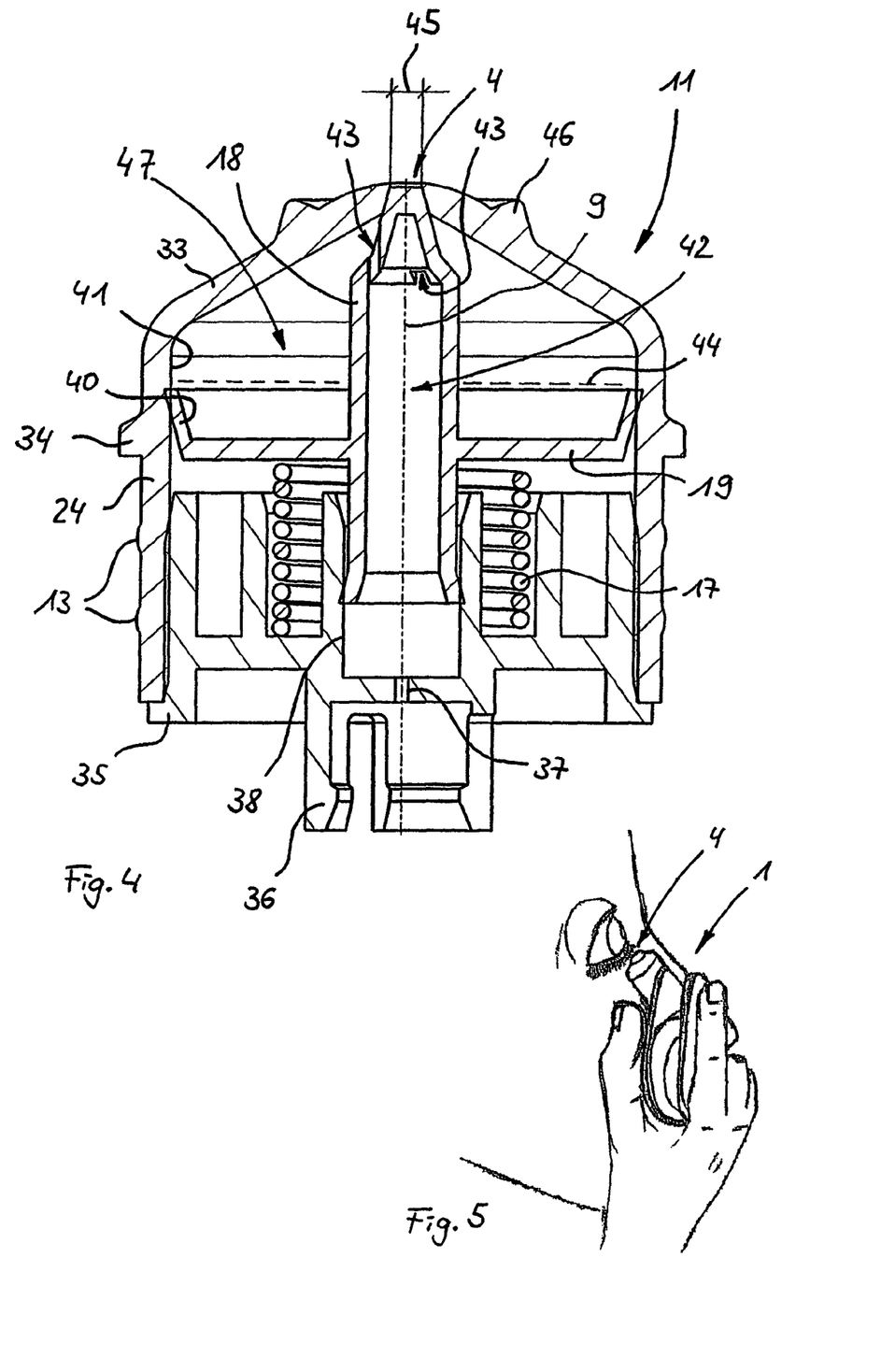
FIG. 4 shows a sectional illustration of the dosing subassembly according to FIG. 2.
FIG. 5 shows an illustration of a dosing operation to the eye of a user with a dispenser according to the invention.

The dispenser 1 illustrated in FIGS. 1 to 4 is, as illustrated in more detail in FIG. 5, a dropper for the dosing of liquid eye drops. The dispenser 1 has a lower holding plate 10, an upper holding plate 6 arranged substantially parallel thereto, and a medium reservoir 2, which is formed by the holding plates 6, 10 and a wall section 5 which is of flexible design and is in the form of a bellows. As illustrated in more detail in FIGS. 2 and 3, the flexible wall section 5, which is designed as a bellows, is molded integrally onto the lower holding plate 10 and has a total of six annular regions 25 which are in each case arranged concentrically opposite one another on a common center axis, are connected integrally to one another and are in the shape of conical sections. The annular regions 25 have a wall thickness of approximately 0.25 mm and are preferably reduced by 50% in wall thickness in connecting zones 26 in order, in the manner of a fixed body hinge, to ensure increased flexibility between the annular regions 25. The lower holding plate 10 and the upper holding plate 6 are respectively provided with recessed grips 27, 28 which can serve as a finger rest, in particular for the thumb and index finger, for single-handed operation of the dispenser 1. A cylindrically shaped dosing nozzle 7 is molded integrally onto the upper holding plate 6, which can be produced in particular from polypropylene, the said dosing nozzle protruding in a raised manner from the surface of the upper holding plate 6 at an angle α of 35 degrees. In a preferred embodiment of the invention, the total of six annular regions 25 of the medium reservoir 2 have an average diameter of approx. 22 mm and a height of in each case approx. 2.2 mm, thus resulting in the medium reservoir having a volume of approx. 5000 mm$^3$ or approx. 5 ml.

As illustrated in more detail in FIGS. 2 and 3, the dosing nozzle 7 has a receiving shaft 29 which is of substantially hollow-cylindrical shape and on the inner wall of which are provided two circularly encircling, axially spaced apart latching grooves 12 for receiving the dosing subassembly 11 with a form fit. A latching pin 14 is arranged symmetrically to a center longitudinal axis 9 of the dosing nozzle 7 and has three latching tongues 15, which are grouped coaxially with respect to the center longitudinal axis 9 at a separation of 120 degrees, for the latching of the dosing subassembly 11 with a form fit. The receiving shaft 29 is connected in a communicating manner with the interior of the medium reservoir 2 via an inflow channel 31 and, upon application of an actuating force to the holding plate 6, 10 and a resultantly caused reduction in the volume of the medium reservoir 2, permits the medium accommodated in the medium reservoir 2 to flow off in the direction of the dosing subassembly 11.

The wall section 5, which is of flexible design, of the lower holding plate 10, which can be produced in particular from polyethylene, is provided with an encircling, dimensionally stable collar 20 which is matched to the geometry of the upper holding plate 6, forms a sealing surface 32 with a lower side of the holding plate 6, which side faces the medium reservoir, and which has, as does the holding plate 6, a tapered, i.e. reduced, wall thickness in an end region. To securely fasten the encircling collar 20 to the upper holding plate 6, a holding ring 22 is injection molded onto the end side in an encircling manner and connects the upper holding plate 6 and the encircling collar 20 in a sealing manner to each other and with a frictional manner and, if appropriate, with a cohesive material joint with respect to the sealing surface 32. For this purpose, the holding ring 22 is provided with a substantially U-shaped cross section, with the end regions of the encircling collar 20 and of the upper holding plate 6 being accommodated between the limbs of the U-shaped cross section of the holding ring 22.

The dosing subassembly 11, which is illustrated in more detail in FIG. 4, has a valve housing 24 designed essentially in the form of a cylindrical sleeve. The valve housing 24 is provided in an end region with a wall section 33 which is at least of substantially spherical design and is penetrated by the dosing opening 4 in the region of the center longitudinal axis 9. On an outer side, the valve housing 24 has two circularly encircling, spaced apart latching lugs 13 which are provided for operative connection to the latching grooves 12 with a form fit in the receiving shaft 29 of the dosing nozzle 7. To facilitate installation and to ensure correct positioning of the dosing subassembly 11 in relation to the dosing nozzle 7, a circularly encircling holding collar 34 is provided on the valve housing 24. The holding collar 34 can enter into operative connection with an end side of the dosing nozzle 7 with a form fit, in order to prevent the dosing subassembly 11 from pressing too deeply into the dosing nozzle 7. A valve support 35 is pressed into the valve housing 24 and, on an end region facing away from the dosing opening 4, has latching tongues 36 which are provided for connection with a form fit—as illustrated in more detail in FIG. 2—to the latching pin 14 of the upper holding plate 6 and are arranged symmetrically with respect to the center longitudinal axis 9. A passage bore 37 arranged in the valve support 35 permits medium to flow from the medium reservoir 2 in the direction of the dosing opening 4. The passage bore 37 is in communicating connection with a receiving bore 38 which is provided for a sliding mounting of the valve pin 18. The valve pin 18 can be displaced along the center longitudinal axis 9 between a rest position (illustrated in FIG. 4) and an opening position (not illustrated), in order to close the dosing opening 4 or to open it up to discharge a medium. The valve support 35 is assigned a circularly encircling receiving groove 39 in which the spring device 17, which is designed as a coiled spring, can be accommodated. The spring device 17 is provided with a pre-stress and exerts a closing force on a plunger sleeve 19, which is assigned to the valve pin 18, in the direction of the dosing opening 4. The plunger sleeve 19 is fitted integrally on the valve pin 18 in a rotationally symmetrical manner and has, in an outer region, a circularly encircling sealing apron 40 that is provided for operative connection to a cylinder wall 41 of the valve housing 24 in a sealing and slidable manner. The valve pin 18 is provided with a cavity 42 which opens into outlet openings 43 which are provided in an end region of the valve pin 18, which region faces the dosing opening 4. There is therefore a communicating operative connection between the medium reservoir 2 and the dosing chamber 47, which is formed by the valve housing 24 and the plunger sleeve 19. The valve pin 18 is of conically tapered design in an end region, with a cone angle of 30 degrees being provided and the smallest diameter of the valve pin being approx. 0.75 mm.

A hydraulic active surface 44 of the plunger sleeve 19 is designed with respect to a cross-sectional area 45 in such a manner that there is a surface ratio of at least 50:1, so that, even if the spring device 17 provides a strong valve closing force, the dosing opening 4 can already be opened by the valve pin 18 at a low pressure. The strong closing force exerted by the spring device 17 on the valve pin 18 ensures the advantageous microbiological sealing of the dosing opening 4 by the valve pin 18.

A circularly encircling drip edge 46 is provided on an outer surface of the valve housing 24, the drip edge having a substantially triangular cross section and forming a sharp edge with respect to the spherically designed region around the dosing opening 4, so that, when a drop of medium is discharged from the dosing opening 4, an advantageous formation of the drop can take place resulting in the drop of medium being dispensed at least substantially without any residue.

The valve pin 18 is of conical design in an end region and protrudes virtually completely into the dosing opening 4, which likewise has a conical contour with respect to the plane of the illustration of FIG. 4. The valve pin 18 therefore ends virtually flush with the spherically designed surface of the wall section 33, so that, when the dosing opening is closed, only a slight depression remains behind in the surface of the wall section 33, in which remaining medium can collect.

As illustrated in FIG. 5, for the dosing of the medium into an eye of the user with the aid of the dispenser 1, an orientation of the holding plates 6, 10 substantially parallel to the cheek area below the user's eye is selected. In this case, the ergonomic design of the dispenser 1 enables the dosing opening 4 to be brought closer to the lower eyelid, so that a drop of medium emerging from the dosing opening 4 can be inserted into the eye in a controlled manner. In the case of the dispenser according to the invention, the controlled insertion is assisted by the single-handed operation and the large supporting surfaces of the holding plates 6, 10 and the great flexibility of the medium reservoir, which is designed in the form of a bellows, and, furthermore, by the valve characteristic of the dosing subassembly 11, which is formed by the extreme surface ratio, and which already permits the dosing opening 4 to be opened up by the valve pin 18 at a low pressure of the medium and therefore assists an advantageous dispensing of the medium.

Figure 6:
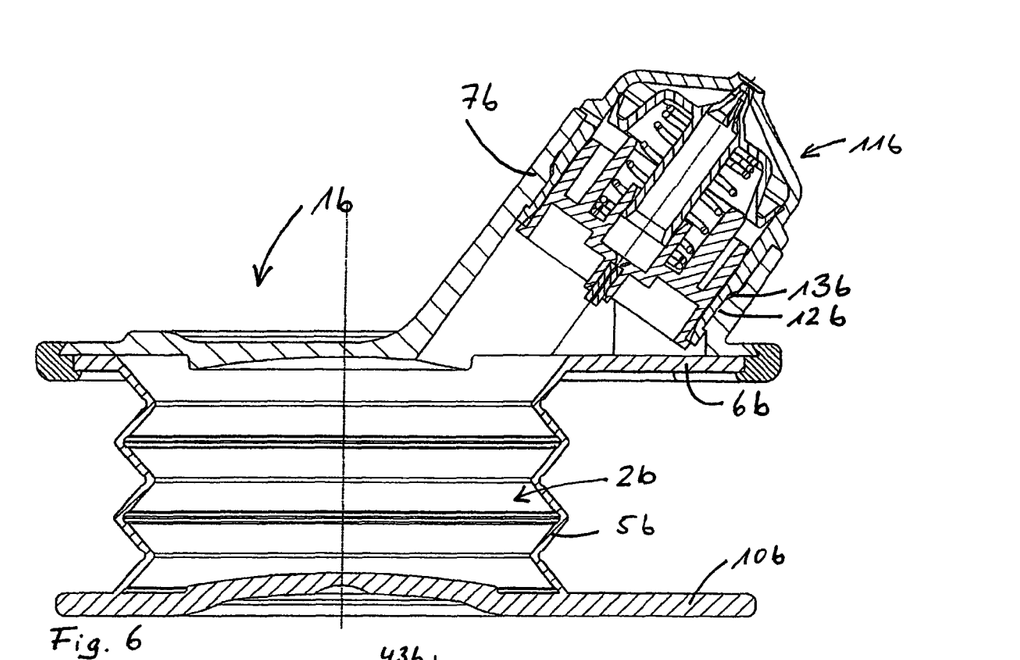
FIG. 6 shows a second embodiment of a dispenser according to the invention in a sectional illustration.
Figure 7:
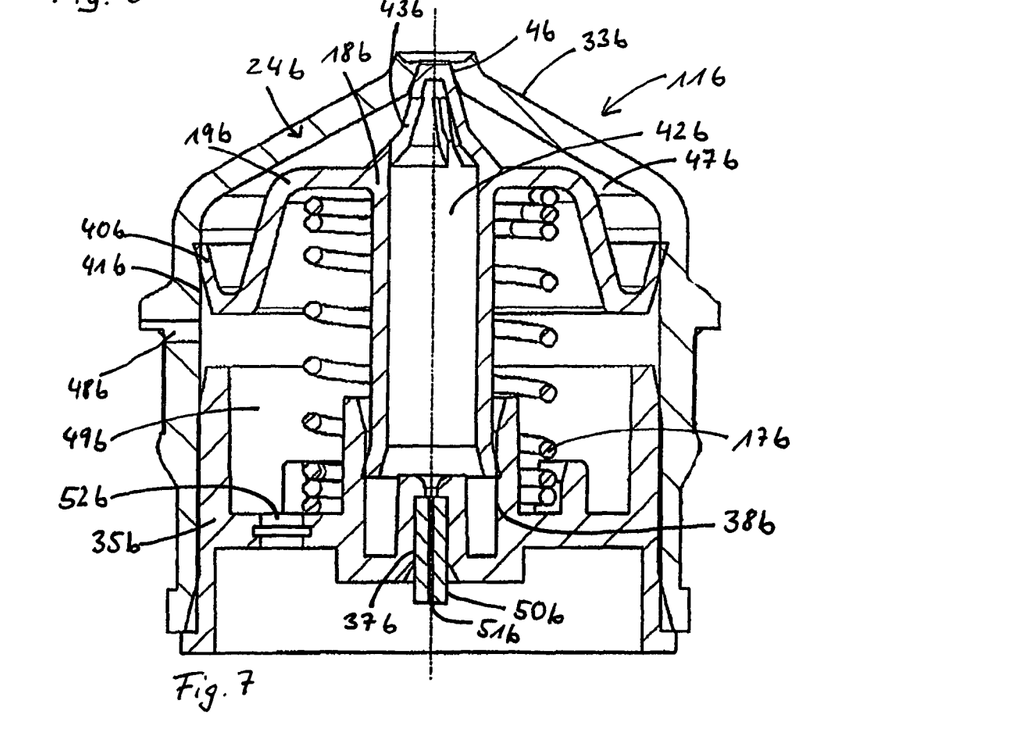
FIG. 7 shows a detailed view of the dosing subassembly, inserted into the dosing nozzle, of the dispenser according to FIG. 6.

FIGS. 6 and 7 show a second embodiment of a dispenser according to the invention. The reference numbers used correspond to the reference numbers of the first embodiment of FIGS. 1 to 4 and are identified by an attached letter b. As can be gathered from FIG. 6, the basic construction of this dispenser 1b is essentially the same as in the first embodiment.

The dispenser likewise has a lower holding plate 10b and an upper holding plate 6b parallel thereto, between which there is a medium reservoir 2b which is closed in the manner of a bellows by the holding plates 6b, 10b and a flexible wall section 5b. The upper holding plate 6b has an inflow channel 31b which provides a passage from the media reservoir 2b to a cylindrical dosing nozzle 7b. This dosing nozzle 7b extends obliquely upward from the upper holding plate 6b. A dosing subassembly 11b, which is explained in more detail in conjunction with FIG. 6, is inserted into the dosing nozzle 7b.

In a departure from the embodiment of FIGS. 1 to 4, the dosing subassembly 11b here is held on the upper holding plate 6b exclusively by latching means 12b, 13b. The latching means 12b, 13b are provided in a manner corresponding to each other on an inner side of the dosing nozzle 7b and on an outer side of the dosing subassembly 11b. On the side of the dosing nozzle, the latching means involves an encircling latching web 12b which engages in a latching depression 13b on the dosing subassembly. A centered latching as by the latching pin 14 in the embodiment of FIGS. 1 to 4 is not provided. This facilitates production and, if the outer latching means 12b, 13b are suitably designed, does not result in any disadvantages.

FIG. 7 shows the dosing subassembly 11b of the second embodiment in a more detailed view. The dosing subassembly 11b also only has slight differences to the dosing subassembly 11 of the embodiment of FIGS. 1 to 4.

The most important components of the dosing subassembly 11b are a valve housing 24b, a valve support 35b, which is inserted into the valve housing 24b and is unmovable relative to the valve housing 24b, and a valve pin 18b, which is inserted between a distal end wall section 33b of the valve housing 24b, on the one hand, and the valve support 35b, on the other hand.

The valve support 35b has a receiving bore 38b which is arranged in a centered manner and interacts with the valve pin 18b. The base of the receiving bore 38b is provided with a receptacle 37b into which a capillary tube 50b is inserted. Medium can flow via a capillary opening 51b of the capillary tube 50b out of the media reservoir 2b through the valve support 35b into the dosing subassembly 18b. The valve pin 18b is of hollow-cylindrical design and, at its end facing the end wall section 33b, is designed such that it tapers conically and is closed. From the valve pin 18b, a plunger sleeve 19b extends radially outward and, molded onto the outer edge thereof, is a sealing skirt 40b which ends in a sealed manner with a cylinder wall 41b of the valve housing 24b. The valve pin 18b is pressed in the direction of the end wall section 33b by a helical spring 17b between plunger sleeve 19b and valve support 35b. The valve pin, with its conical end in a dosing opening 4b of likewise conical design, bears against the end wall section 33b and closes the dosing opening in a microbiologically tight manner. Furthermore, the valve pin 18b ends with its opposite end in a radially encircling and tight manner with the receiving bore 38b of the valve support 35b. In the region of its conical end, the valve pin 18b has an aperture 43b through which rapid equalization of the pressure between a cavity 42b in the valve pin 18b and a dosing chamber 47b formed by the plunger sleeve 40b and the end wall section 33b is possible.

In the cylinder wall 41b of the valve housing 24b there is provided an aperture 48b through which an ambient pressure chamber 49b, which is arranged between the plunger sleeve 40b and the valve support 35b, connected to the surroundings in a manner free from pressure differential. Furthermore, the ambient pressure chamber 49b is connected via an aperture 52b to the media reservoir 2b. A filtering membrane is inserted into this aperture and permits a slow equalization of the pressure between the ambient pressure chamber 49b and the surroundings, on the one hand, and the media reservoir 2b, on the other hand. The filtering membrane furthermore serves to microbiologically seal the media reservoir 2b. Ambient air flowing into the media reservoir 2b via the ambient pressure chamber 49b is cleaned, thus avoiding a contamination of the medium in the media reservoir 2b.

When the dispenser 1b is actuated, medium enters the cavity 42b and the dosing chamber 47b. At the same time, the pressure in the media reservoir 2b, in the cavity 42b and in the dosing chamber 47b rises. In the meantime, the pressure in the ambient pressure chamber 49b remains constant. The medium does not emerge through the aperture 52b, since the latter is formed in such a manner that the media liquid present cannot pass through it.

The pressure differential between the dosing chamber 47b and the ambient pressure chamber 49b causes the valve pin 18b together with the plunger sleeve 40b to be displaced in the direction of the valve support 35b. By this means, the dosing opening 4b is opened up by the disengaging conical end of the valve pin 18b and the medium contained in the dosing chamber 47b can emerge. The capillary opening 51b in the capillary tube 50b ensures that, even in the event of a very vigorous actuation, a restriction of the throughflow quantity is obtained. The capillary opening 51b here acts as a throttle. The capillary tube 50b with the capillary opening 51b therefore serves the same purpose as the simple passage bore 37 as in the embodiment of FIGS. 1 to 4. However, the use of a capillary tube has the advantage that difficult production of the fine bore is avoided and instead only a less complicated receptacle 37b for the premanufactured capillary tube 50b has to be provided. In addition, the use of different capillary tubes makes it possible to obtain a very simple adaptation of the dispenser to different types of media and intended uses.

After the discharging operation has ended, a negative pressure prevails in the media reservoir because of the volume of medium which has escaped, the negative pressure being equalized again by means of air flowing through the aperture 52b and the filtering membrane inserted therein.

In an embodiment (not illustrated) of the invention, an integral design of the medium reservoir with the two holding plates and the dosing nozzle provided on the one holding plate is realized. A medium reservoir of this type can be produced in particular by blow molding or gas injection, wherein, if appropriate, a redesigning of the medium reservoir illustrated in FIGS. 1 to 5 to match the single-part production being undertaken.

In a further embodiment (not illustrated) of the invention, instead of the dosing subassembly, an elastic valve element is provided in the end of the dosing nozzle. The elastic valve element, which can be produced in particular from a highly elastic material, such as silicone, is enclosed by a wall of the dosing nozzle and can be designed in particular as a plate-like slotted valve. For this purpose, one or more slots, in particular oriented orthogonally to one another, are cut into a rectangular, polygonal or circular plate of the highly elastic material. The incisions are of such thin design that the cut surfaces bear in a sealing manner against one another and only when a positive pressure is applied on one side does an arching of the plate take place, leading to the slot or the slots opening. With the aid of a valve element of this type, a reliably closing, simply constructed dosing valve can be realized for the above-described dispenser. In a particularly preferred embodiment of the invention, the elastic valve element is accommodated in a valve housing and can be inserted instead of the dosing subassembly into the dosing nozzle.

The invention claimed is:

1. Dispenser for at least one liquid or pulverulent, the dispenser including a medium reservoir provided for single-handed operation and a dosing opening, the medium reservoir being bounded at least in some sections by wall sections of flexible design and by at least one dimensionally stable holding plate provided as a handle for the application of actuating forces to the medium reservoir, the dosing opening being formed on a dosing nozzle, the dosing nozzle having a center longitudinal axis arranged at an angle of 35 degrees relative to an outer surface of the holding plate in order to ensure ergonomic handling of the dispenser.

2. Dispenser according to claim 1, wherein the dosing opening is provided in a separate dosing subassembly fitted on the dosing nozzle, the dosing nozzle being assigned to the holding plate and configured as a receiving shaft.

3. Dispenser according to claim 2, including at least one centrally arranged latching device for locking the dosing subassembly with a form fit in the dosing nozzle.

4. Dispenser according to claim 3, wherein the latching device has at least one latching geometry on at least one of an inner surface and an outer surface of the dosing nozzle and a latching pin arranged coaxially with respect to the center longitudinal axis of the dosing nozzle, the latching geometry and latching pin being provided for centering and fixing the dosing subassembly in the dosing nozzle.

5. Dispenser according to claim 2, wherein the dosing subassembly has a spring-loaded outlet valve for temporarily closing the dosing opening.

6. Dispenser according to claim 2, wherein a drip edge for conducting away drops of medium without any residue is provided on the dosing nozzle or the dosing subassembly in the region of the dosing opening.

7. Dispenser according to claim 1, wherein the medium reservoir is bounded by two dimensionally stable holding plates arranged opposite each other, the dosing nozzle being assigned to one of the holding plates.

8. Dispenser according to claim 1, wherein the medium reservoir is formed integrally with the holding plate.

9. Dispenser for at least one liquid or pulverulent, the dispenser including a medium reservoir provided for single-handed operation and a dosing opening, the medium reservoir being bounded at least in some sections by wall sections of flexible design and by at least one dimensionally stable holding plate provided as a handle for the application of actuating forces to the medium reservoir, the dispenser further including a dimensionally stable collar coupled to the holding plate, the collar being provided on a peripheral edge region of one of the wall sections of the medium reservoir, the edge region facing the holding plate.

10. Dispenser according to claim 9, further including a peripheral holding ring for coupling the holding plate to the collar with a form fit, the holding ring engaging around respective end regions of the holding plate and the collar and coupling the end regions to each other in a sealing manner.

11. Dispenser according to claim 10, wherein the end regions of the holding plate and the collar are each provided with a reduced wall thickness, and the holding ring is molded onto the end regions to provide a cohesive material joint between the holding ring and the end regions.

12. Dispenser for at least one liquid or pulverulent, the dispenser including a medium reservoir provided for single-handed operation and a dosing opening, the medium reservoir being bounded at least in some sections by wall sections of flexible design and by at least one dimensionally stable holding plate provided as a handle for the application of actuating forces to the medium reservoir, the dispenser further including pressure equalizing means for permitting ambient air to flow into the media reservoir, the pressure equalizing means being arranged in a wall region of the media reservoir such that the pressure equalizing means is surrounded on the media reservoir side by medium when the dispenser is actuated.

13. Dispenser according to claim 12, wherein the pressure equalizing means includes a filtering membrane for filtering microbiological impurities.

14. Dispenser for at least one liquid or pulverulent, the dispenser including a medium reservoir provided for single-handed operation and a dosing opening, the medium reservoir being bounded at least in some sections by wall sections of flexible design and by at least one dimensionally stable holding plate provided as a handle for the application of actuating forces to the medium reservoir, the wall sections of the medium reservoir being produced at least in some sections as a bellows of polyethylene with a wall thickness of 0.25 mm to 0.5 mm, and the medium reservoir is provided in the region of the bellows, on at least one of an inner and an outer surface of the medium reservoir, with a water vapor barrier layer in the form of a silicon oxide coating or a poly-para-xylylene coating.

* * * * *